United States Patent [19]

Pitha et al.

[11] Patent Number: 5,110,927
[45] Date of Patent: May 5, 1992

[54] PRAZOSIN ANALOG WITH INCREASED SELECTIVITY AND DURATION OF ACTION

[75] Inventors: Josef Pitha, Baltimore; John W. Kusiak, Lanham/Seabrook, both of Md.

[73] Assignee: The United States of America as represented by the Department of Health and Human Services, Washington, D.C.

[21] Appl. No.: 140,744

[22] Filed: Dec. 31, 1987

[51] Int. Cl.$^5$ ............................................. C07D 403/04
[52] U.S. Cl. ......................................................... 544/291
[58] Field of Search .................................. 544/292, 291

[56] References Cited

U.S. PATENT DOCUMENTS

| | | | |
|---|---|---|---|
| 4,092,315 | 5/1978 | Blanco | 544/291 |
| 4,130,647 | 12/1978 | Taylor | 544/291 |
| 4,197,301 | 4/1980 | Smith et al. | 544/291 |
| 4,310,524 | 1/1982 | Wiech et al. | 514/222 |
| 4,472,380 | 9/1984 | Harris et al. | 546/156 |
| 4,532,135 | 7/1985 | Edwards | 514/222 |
| 4,601,897 | 7/1986 | Saxton | 514/260 |

OTHER PUBLICATIONS

Takayanagi, et al., "Chemical Abstracts," vol. 104, 1986, col. 104:45639x.
Helman, et al., "Chemical Abstracts," vol. 106, 1987, col. 106:113446a.
Shiraishi, et al, "Chemical Abstracts," vol. 107, 1987, col. 107:183590m.
Arch. Int. Pharmacodyn. 240: 305-313 (1979).
Arch. Int. Pharmacodyn. 245: 218-235 (1980).
New Zealand Med. Journal 94: (1981) 67.

Primary Examiner—C. Warren Ivy
Assistant Examiner—James H. Turnipseed

[57] ABSTRACT

Alkylating analogs of prazosin were synthesized and found to compete with nanomolar potency at $^3$H-prazosin binding sites of rat tissues. The compounds were found to be irreversible ligands at $^3$H-prazosin binding sites, and denoted a subtype of alpha$_1$-adrenoceptors.

3 Claims, 4 Drawing Sheets

3H-PRAZOSIN BOUND, fmol/mg protein

PRAZOSIN ANALOG WITH INCREASED SELECTIVITY AND DURATION OF ACTION

FIELD OF THE INVENTION

The present invention relates to improved antihypertensive therapy, and more particularly to a new prazosin analog which is more selective and durable than prazosin itself.

BACKGROUND OF THE INVENTION

Prazosin, the hydrochloride salt of 2-(4-(2-furoyl)-piperazine-1-yl)-4-amino-6,7-dimethoxy-quinazoline, compound 1 of Table I wherein R is 2-furoyl, is an antihypertensive agent with a chemical structure unrelated to that of any other in use.

Since its introduction, prazosin remains the drug of choice both in human therapy and in laboratory studies of alpha$_1$-adrenoreceptors. Many analogs of prazosin have been prepared and patented since that time.

Side effects of a drug are caused by a lack of specificity in drug-receptor interaction. Nearly all drugs interact with several classes of receptors, and thus have multiple effects on physiology, some of which represent undesirable side effects of therapy. Thus, compounds with increased selectivity towards drug receptors are sought that possibly may permit more selective intervention in the organism.

Prazosin has been shown to lower blood pressure in hypertensive patients and in normotensive and hypertensive animals. The mechanism of action of prazosin is presently believed to be based upon a relaxation of peripheral arterioles as a consequence of a functional inhibition of alpha$_1$-adrenoceptors. Prazosin exhibits a preferential affinity for postsynaptic alpha$_1$-adrenoreceptors, designated as alpha$_1$.

Considerable progress has recently been achieved in understanding alpha$_1$-adrenoreceptor structures. For studies on chemical modification of alpha$_1$-adrenoceptors, phenoxybenzamine, N-ethoxycarbonyl-2- ethoxy-1,2-dihydroquinoline (EEDQ), and so-called tetramine disulfides have been used. However, there are a number of disadvantages to the use of these compounds. Phenoxybenzamine is not very specific; in addition to alpha$_1$-adrenoceptors, it interacts with alpha$_2$-adrenoceptors, histamine receptors, dopamine receptors, and muscarinic receptors. The receptor specificity of N-ethoxycarbonyl-2-ethoxy-1,2-dihydroquinoline is also low. In addition this compound must be used at concentrations about 10$^4$ higher than the more specific chemoreactive labels. The tetramine disulfide, pyrextramine, was used to selectively block peripheral alpha$_1$-adrenergic responses. However, more recently, pyrextramine was shown to block peripheral alpha$_2$-adrenergic responses as well, which suggests a lack of specificity for alpha$_1$-adrenergic responses.

The importance of events mediated by alpha$_1$-adrenoceptors is well recognized, including their role as targets for drugs and neurotransmitters initiating the breakdown of phosphoinositides. Much work has been directed at characterizing the alpha$_1$-adrenergic binding site. Photoaffinity probes developed and studies by several groups showed specific incorporation of iodinated ligands into a peptide of approximately 80,000 mwt. Other studies have examined the metabolism of alpha$_1$-adrenoceptors both in vivo and in cultured cells, using phenoxybenzamine.

SUMMARY OF THE INVENTION

It is an object of the present invention to overcome deficiencies in the prior art.

It is a further object of the invention to provide for improved antihypertensive therapy.

It is another object of the present invention to provide analogs of prazosin which are more selective than any prior known analog.

It is yet a further object of the present invention to provide prazosin analogs which bind strongly and persistently to alpha$_1$-adrenoreceptors, but even at high concentrations are unable to occupy all alpha$_1$-adrenoceptors which bind prazosin. The prazosin analogs investigated have the following structural formulae:

(I)

wherein R is as defined in Table I; compound No. 1 is prazosin itself; compound 47 fulfills all the above requirements while compound 48 behaves similarly to 47 in those aspects which were investigated.

The other derivatives which are part of the present invention may have a bicycloalk-2-ene-2-carboxyl on the N' substituent, which may contain additional double bonds or may be oxa, thia, or aza derivatives thereof.

The compounds of the present invention are useful as tools for studying the alpha$_1$-adrenoceptors, i.e., the drug receptor to which prazosin binds. Of these compounds, number 47 and its derivatives wherein the bicyclooctadiene residue is replaced by any other bicycloalkane residue containing at least one double bond, or by an oxa thia, or aza derivative thereof, have been found to have markedly useful properties in these studies. The compounds of the present invention provide an affinity labelling compound with high specificity for alpha$_1$-adrenoceptors which can be utilized both in vitro and in vivo. The compounds of the present invention are irreversible when used in membrane preparations and when injected intraperitoneally into a host. Unexpectedly, these compounds apparently delineate a subset of $^3$H-prazosin binding sites.

Figure 1:
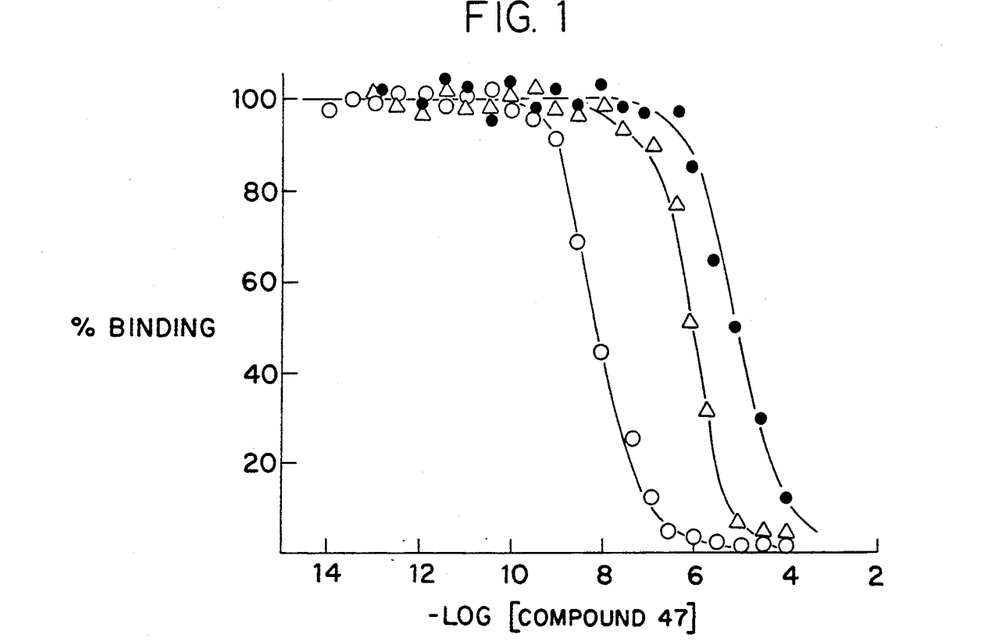
Figure 2:
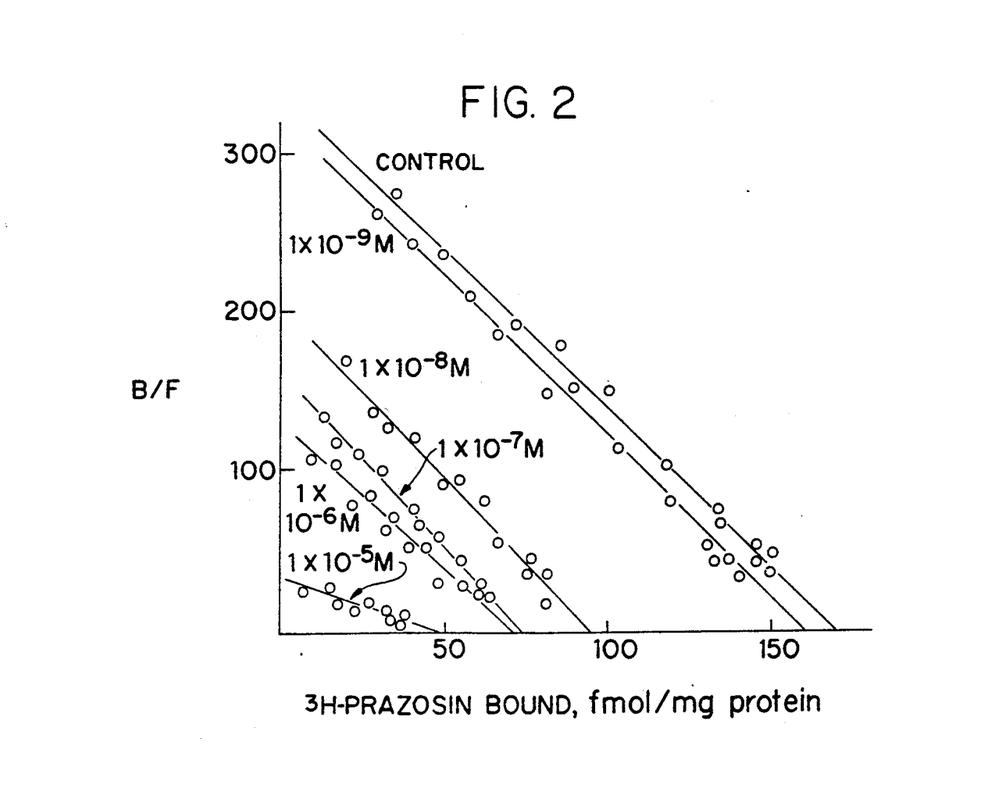

The compounds of the present invention have a nanomolar potency for alpha$_1$-adrenoreceptors in various rat membrane preparations, and in brain membrane preparations those tested of these compounds displaced $^3$H-DHA and $^3$H-yohimbine only at high concentrations, as seen in FIG 1. They are about 250-fold selective for alpha$_1$- versus alpha$_2$-adrenoreceptors. They appear to persistently block $^3$H-prazosin binding sites. Preincubation of membranes with the tested compounds followed by extensive washing led to a 50% reduction in the concentration of $^3$-prazosin binding sites, as shown in FIG. 2. Membranes treated in an identical manner did not exhibit any decrease in $^3$-DHA or $^3$-yohimbine binding, again suggesting the specificity of this ligand for alpha$_1$-adrenoceptors, cf. FIG. 5.

Compound 47 contains an alpha, beta-unsaturated carbonyl group which has the potential to react chemically with some of the amino acyl residues of react chemically with some of the receptor, e.g., cysteine.

Such a chemical reaction would bind the drug to the receptor permanently, and the effects of the drug should be quite persistent. Additionally, the combination of the chemical reaction and the normal interaction with the receptor may give the drug extra selectivity, i.e., only some of the receptors may possess both the interaction and reaction sites. Both the persistence and selectivity of the compound were detected, as is shown below.

Figure 3:
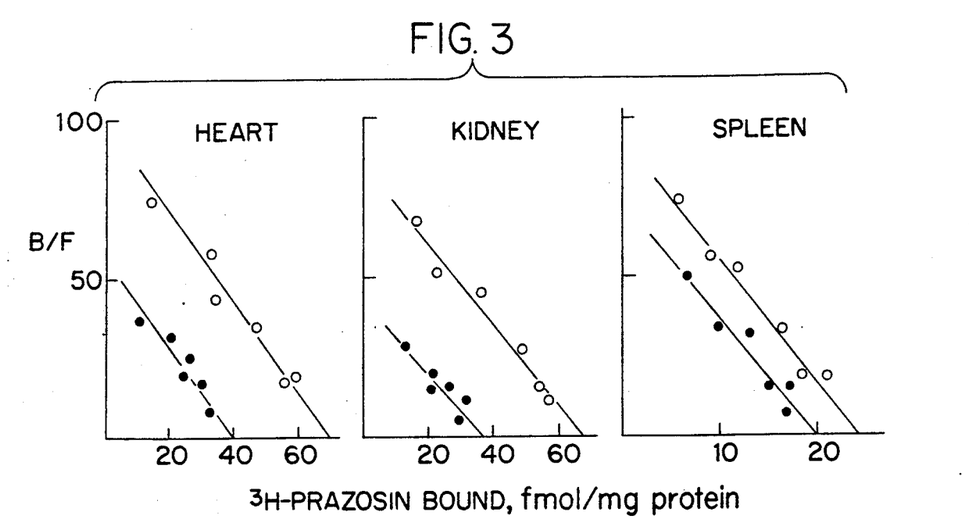
FIG. 3 - Blockage of different rat tissue $^3$H-prazosin binding sites by compound No. 47. Membranes were pretreated without 0---0, or with 0---0 $1 \times 10^{-7}$M of compound No. 47, washed and assayed for saturation of $^3$-prazosin binding. Data are from representative experiments repeated three separate times.
Figure 4:
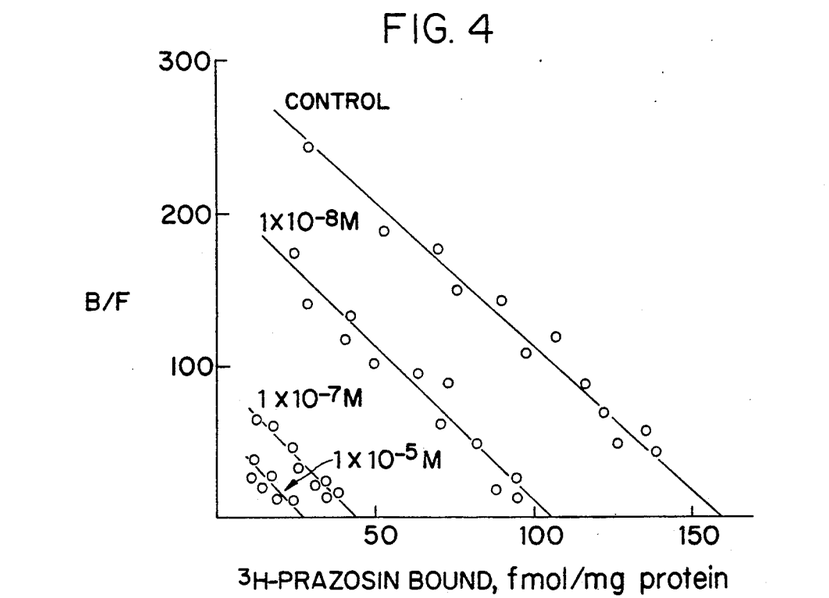
FIG. 4 - In vitro blockade of rat brain $^3$-prazosin binding sites by phenoxybenzamine. Membranes were preincubated with phenoxybenzamine and processed as described in the Methods. Data are the average of three separate experiments varying less than 10% from the average.

The compounds of the present invention are active in animals. Intraperitoneal injection led to a reduction in $^3$-prazosin binding sites in membranes from various organs prepared sixteen hours afterwards. The Kd values were unchanged, except in kidney, suggesting the irreversible nature of this interaction with receptors. The compounds resemble phenoxybenzamine in certain characteristics. They are both irreversible ligands at alpha$_1$-adrenoceptors, as shown in FIGS. 2–4, and they are both active in vivo. They both appear to be relatively selective for alpha$_1$-adrenoceptors, the compounds of the present invention more than phenoxybenzamine. They differ in one respect, in that phenoxybenzamine appears to block almost all $^3$-prazosin binding sites in brain membranes and in other tissues as well, whereas the compound of the present invention blocks only about one-half of the receptors in brain tissue, both in membrane preparations and after injections in vivo, suggesting the possibility of subclasses of $^3$-prazosin binding sites.

Figure 7:
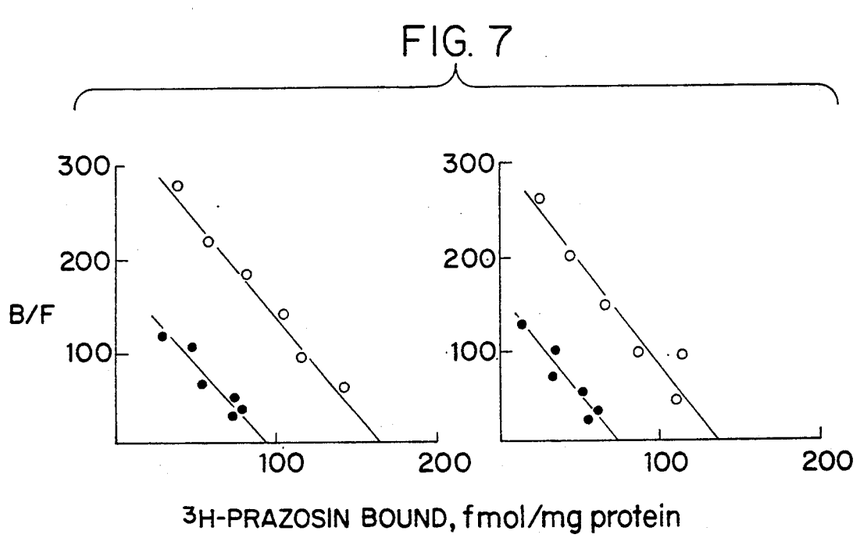
FIG. 7 - Effect of a double preincubation of rat brain membranes with compound 47 on the blockade of $^3$-prazosin binding sites. Membranes were preincubated without 0---0, or with 0---0 $1 \times 10^{-7}$M of compound No. 47, diluted, and washed three times as described in the Methods. One-half of each membrane fraction was assayed for $^3$-prazosin binding. The other half was resuspended in its original volume and incubated a second time without or with $1 \times 10^{-7}$M of compound No. 47. Membranes were then diluted, washed three more times, resuspended, and assayed for saturation of $^3$-prazosin binding. The data are the average of three separate experiments.

A number of control experiments were performed to substantiate the possibility of subclasses of $^3$-prazosin binding sites. Brain membranes were preincubated with the compound of the present invention, washed extensively, and then subjected to another round of preincubation with the compound and washing before assaying for saturation of $^3$-prazosin. In this case, no further blockade of receptors was noted, as shown in FIG. 7. This result would suggest that the compound of the present invention was not being metabolized or consumed in the preincubation, thereby preventing its interaction with all available alpha$_1$ sites.

Furthermore, increasing the ratio of absolute amounts of ligand to receptor by 10- or 100-fold did not enhance the blockade of $^3$-prazosin binding sites. In the standard preincubation, the ratio of the compound of the present invention, hereinafter designated as compound 47, (100 nM), to receptor was 50:1. The preincubation of membranes with compound No. 47 at higher ratios of ligand to receptor only decreased the concentration of ligand by 10- and 100-fold, respectively, at which the large Kd effects were noted, as shown in FIG. 2.

Figure 6:
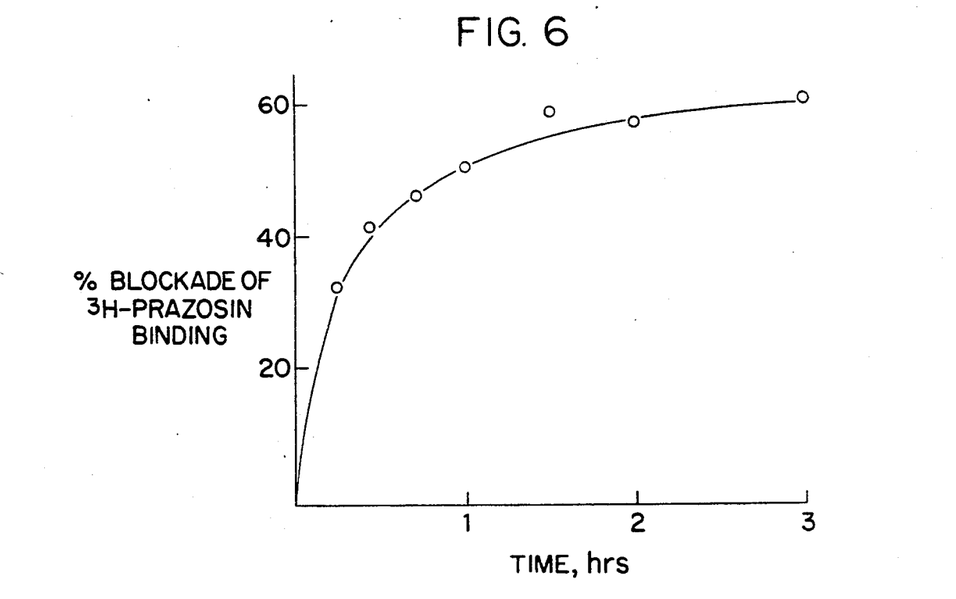
FIG. 6 - Effect of preincubation time on blockade of $^3$-prazosin binding sites by compound 47. Pairs of membrane fractions were preincubated without or with $1 \times 10^{-8}$M of compound No. 47 for various times between 15 min and 3 hr before washing and resuspension for assay of saturation of $^3$-prazosin binding. $B_{max}$ values were determined from Scatchard plots and are presented as % blockade versus time matched controls. The data are the average of two separate experiments.

The effect of preincubation time on the amount or irreversible blockade was determined to assure that compound No. 47 had reacted completely with available sites, cf. FIG. 6. In these experiments, blockade reached a maximum value after about 45 minutes of preincubation, and remained at this level even after three hours of preincubation. This experiment showed that compound No. 47 was very reactive with binding sites, and that an incomplete reaction was not the reason for partial blockade.

In some cases, the entire set of procedures, from membrane preparation through preincubation, washing, and assaying of $^3$H-prazosin was carried out in different buffers, either 1 mM Tris, pH 7.4, or 50 mM sodium phosphate, pH 7.2, to make sure, at least with the Tris buffer, that all binding sites were available to interact with compound No. 47. The use of 1 mM Tris would preclude, in closed vesicles (synaptosomes), the presence of binding sites which were inaccessible to compound No. 47. The finding of similar blockade with phosphate buffer indicated that compound No. 47 was not reacting with Tris buffer. Finally, 100 microM (−)epinephrine was used instead of phentolamine to identify non-specific binding in saturation experiments. No difference in blockade by compound No. 47 was noted, suggesting that a portion of biologically important receptors were being blocked.

Treatment of membranes prepared from rat brains with prazosin decreased the number of alpha$_1$-adrenoceptors measurable there. Washing the prazosin from the membranes restored the number of alpha$_1$-adrenoceptors on the membranes. Analogous treatment by alkylated prazosin (compound No. 47) decreased the number of alpha$_1$-adrenoceptors permanently, i.e., receptors could not be regenerated by washing the drug from the membranes.

Additionally, the effects of alkylated prazosin are selective. Only approximately one half of the alpha$_1$-adrenoceptors could be eliminated in a clean manner. To eliminate additional receptors, such high concentration of alkylated prazosin had to be applied that the receptor and other proteins of the membrane preparation were modified non-selectively. These findings indicate that alpha$_1$-adrenoceptors, using alkylated prazosin as a probe, may be further subdivided into two distinct groups. This type of subdivision may eventually be used to obtain more selective therapeutic intervention.

The same membrane system was also used to establish that treatment with alkylated prazosin did not introduce permanent change in the numbers of alpha$_2$- and beta-adrenoceptors.

Using dispersed cells from rat salivary glands (parotid), it was established that alkylated prazosin potently inhibited the efflux of calcium ions which was activated by catecholamines. Treatment by alkylated prazosin, on the other hand, did not interfere in the efflux of calcium ions when the efflux of calcium ions was activated by the cholinergic (muscarinic) hormonal system.

The distinctive and useful properties of alkylated prazosin observed on the above simple levels were sustained at the level of animal and tissue preparations, as further described later on in the present specification.

The prazosin analogs of the present invention were prepared by acylation of 4-amino-6,7-dimethoxy-2-(piperazin-1-yl)quinazoline with acyl chlorides, isocyanatanes, or isothiocyanatanes. The structures of the compounds are shown in Table 1 and their chemical characterization in Table 2. The required piperazine derivative was an intermediate in the originally used industrial synthesis of prazosin, and was obtained either by a modification of the method or by acid hydrolysis of prazosin.

TABLE I

Effects of Analogs on $\alpha_1$-Adrenoceptor Binding of $^3$H-Prazosin

| no. | R | $-\log IC_{50}$ | irreversibility ($B_{max}$ decrease) |
|---|---|---|---|
| 1 | -2-furoyl | 9.79 | (−) |
| 2 | —CO-1-imidazolyl | 7.97 | N.T.[a] |
| 3 | —CO—CH$_2$Br | 5.27 | N.T. |
| 4 | —CO—CH=CH—COOCH$_3$ (trans) | 9.15 | (−) |
| 5 | —CO—CH=CH—CH=CH—COOCH$_3$ (trans, trans) | 8.01 | (−), $K_D$ effect |
| 6 | —CO—CH=CH—CH=CH—CH$_3$ (trans, trans) | 8.81 | (−) |
| 7 | —CO—CH$_2$—CH$_2$—C$_6$H$_5$ | 8.47 | N.T. |
| 8 | —CO—CH$_2$—O—C$_6$H$_5$ | 7.90 | N.T. |
| 9 | —CO—CH=CH—C$_6$H$_5$ (trans) | 9.16 | (−), $K_D$ effect |
| 10 | —CO—CH=CH-p-C$_6$H$_4$—F (trans) | 7.92 | N.T. |
| 11 | —CO—CH=CH-p-C$_6$H$_4$—Cl | 7.90 | N.T. |
| 12 | —CO—CH=CH-p-C$_6$H$_4$—Br | 7.10 | N.T. |
| 13 | —CO—CH=CH-m-C$_6$H$_4$—F | 7.68 | N.T. |
| 14 | —CO—CH=CH—C$_6$F$_5$ | 6.94 | N.T. |
| 15 | —CO—CH=CH-p-C$_6$H$_4$—OCH$_3$ (trans) | 8.47 | (−) |
| 16 | —CO—CH=CH-p-C$_6$H$_4$—N$_3$ (trans) | 9.49 | (+), UV light |
| 17 | —CO—CH=CH-p-C$_6$H$_4$—NCS | 6.99 | N.T. |
| 18 | —CO—CH=CH-p-C$_6$H$_4$—NH—CO—CH$_2$Br (trans) | 6.97 | (−), $K_D$ effect |
| 19 | —CO—CH=CH-p-C$_6$H$_4$—NH—CO—CH=CH—COOCH$_3$ (trans, trans) | 7.79 | (−) |
| 20 | —CO—CF=CH—C$_6$H$_5$ | 7.89 | (−) |
| 21 | —CO—CN$_3$=CH—C$_6$H$_5$ | 8.06 | (−) |
| 22 | —CO—C(C$_6$H$_5$)=CH—C$_6$H$_5$ | 7.51 | N.T. |
| 23 | —CO—CH=CH—CO—C$_6$H$_5$ (trans) | 7.06 | N.T. |
| 24 | —CO-2-naphthyl | 7.31 | N.T. |
| 25 | —CO—CH—(CH$_2$)—CH—C$_6$H$_5$ (trans) (cyclopropane) | 9.29 | N.T. |
| 26 | —CO—CH—(O)—CH—C$_6$H$_5$ (trans) (epoxide) | 7.45 | (−) |
| 27 | —CO—CH—(C(CH$_3$)$_2$)—CH—CH=C(CH$_3$)$_2$ (cis + trans) | 7.15 | N.T. |
| 28 | —CO—C≡C—C$_6$H$_5$ | 7.92 | N.T. |
| 29 | —CS—NH—C$_6$H$_5$ | 11.16 | N.T. |
| 30 | —CS—NH—C$_6$H$_{11}$ | 8.27 | N.T. |
| 31 | —CS—NH-p-C$_6$H$_4$—F | 8.62 | N.T. |
| 32 | —CS—NH—C$_6$F$_5$ | 7.80 | (−) |
| 33 | —CS—NH-p-C$_6$H$_4$—N$_3$ | 7.70 | N.T. |
| 34 | —CS—NH-p-C$_6$H$_4$—NCS | 7.18 | N.T. |
| 35 | —CS—NH-m-C$_6$H$_4$—NCS | 7.30 | N.T. |
| 36 | —CS—NH-p-C$_6$H$_4$—NH—CS—N(CH$_2$)(CH$_2$) (aziridinyl) | 7.01 | N.T. |
| 37 | —CS—NH-p-C$_6$H$_4$—CH=CH—COOCH$_3$ | 7.43 | N.T. |
| 38 | —CS—NH-1-naphthyl | 7.41 | N.T. |
| 39 | —CO—NH—C$_6$H$_5$ | 7.56 | N.T. |
| 40 | —CO-m-C$_6$H$_4$—CH$_2$Cl | 7.93 | N.T. |
| 41 | —CO—C$_6$H$_3$-m-I-p-NCS | 7.29 | N.T. |
| 42 | —CO—CH$_2$—CH$_2$—CH$_2$—CH$_2$-p-C$_6$H$_4$—NH—CO—CH=CH—COOCH$_3$ (trans) | 8.07 | (−) |
| 43 | —SO$_2$-p-C$_6$H$_4$—CH$_3$ | 7.94 | N.T. |
| 44 | —SO$_2$-2-thienyl | 7.47 | N.T. |
| 45 | —CO-2,4-dichloro-6-pyrimidinyl | 7.49 | N.T. |
| 46 | —CO-bicyclo[2.2.1]hept-2-ene-5-yl | 8.61 | (−) |
| 47 | —CO-bicyclo[2.2.2]octa-2,5-diene-2-yl | 7.99 | (+) |
| 48 | —CO-bicyclo[2.2.2]octa-2-ene-2-yl | 8.4 | (+) |

[a]Not tested.

The ability of the compounds of the present invention to compete with $^3$-prazosin for binding sites on rat cerebral cortical membranes was measured, and IC50 values were calculated from the displacement curves. A broad range of affinities was found spanning about six orders of magnitude. The results of this are found in Table 1.

Preincubation of membranes with respective compounds from this series, followed by extensive washing and then assaying for saturation of specific $^3$-prazosin binding established whether these compounds were irreversibly bound to receptor sites. Of all the compounds tested in this manner, only compound 47 appeared to be irreversible. Scatchard plots of saturation of $^3$-prazosin binding after preincubation with compound 47 indicated a decrease in the relative number of sites (Bmax) without a change in the affinity (KD) of the remaining sites. Compound 47 retained the alpha$_1$ specificity of prazosin, since its affinity at $^3$-yohimbine binding sites on brain membranes was over a hundred times lower than at $^3$-prazosin binding sites and compound 47 did not irreversibly block $^3$-yohimbine binding sites when preincubated with membranes. Some of the other compounds, while not irreversible, did have some anomalous persistent effects, the results of which are shown in Table 1.

The preparation of a chemoreactive label based on the prazosin pharmacophore proved to be difficult, as over fifty compounds were prepared and tested before an acceptable label was obtained. Many modifications of the prazosin structure led to compounds with drastically reduced affinity to alpha$_1$-adrenoceptors. Furthermore, some compounds with high affinity and with a chemoreactive group had no specific chemical reactivity towards the receptor.

From a structural point of view, the compounds can be divided into six groups, as shown in Table 1. The first group has one member, compound 2, in which the furan nucleus of prazosin was replaced by the isosteric heterocycle, imidazole. Compounds of this type are chemically reactive towards amino groups and were used as affinity labels. Unfortunately, unexpectedly, compound 2 had low affinity.

In the second group of compounds, the furan nucleus of prazosin was replaced by aliphatic groups. Introduction of a bromoacetyl group, which was successfully used in beta-adrenergic ligands, yielded compound 3, which had low affinity. The unsaturated acyl groups (compounds 4–6), which were successfully used in studying opioid receptors, yielded some compounds of high affinity, such as compound 6, but which did not irreversibly block alpha$_1$-adrenoceptors.

The third group of compounds have a cinnamoyl residue. The cinnamoyl analog of prazosin, compound 9, has previously been shown to be capable of reducing blood pressure in conscious, spontaneously hypertensive rats, and on this basis an effective cinnamoyl type photoprobe for alpha$_1$-adrenoceptors was designed. However, the present results show that when the trans double bond of the cinnamoyl residue is replaced by a single bond, as in compounds 7 and 8, affinity is considerably decreased. Also, replacement by a triple bond leads to decreased affinity. If the double bond of a cinnamoyl residue is conserved as a part of an additional cyclic structure, as in the naphthalene derivative, compound 24, the affinity is also decreased considerably. A cyclopropane moiety may be considered a homolog of a double bond, and this reasoning appears to be the case here. The cyclopropane derivative, compound 25, has an affinity similar to that of the cinnamoyl compound No. 9. Ethylene oxide has obvious similarity to cyclopropane, and the chemoreactivity required of irreversible labels. Unfortunately, when an oxirane analog, compound 26, was made, its affinity for receptors was two orders of magnitude lower than that of cyclopropane.

Obviously, polar or hydration effects are of importance. There are obvious limitations to substitution of the cyclopropane ring as well: a derivative of chrysanthemic acid, compound 27, had very low affinity. Substitutions on the double bond of the cinnamoyl residue, compounds 20–22, or insertion of a carbonyl between the double bond and phenyl residue, compound 23, also reduced affinity considerably. In compounds 10–19, the phenyl ring of the cinnamoyl residue was modified. Decreased affinities were observed with the single exception of a p-azido derivative, compound 16.

The fourth group investigated consisted of thioureas and ureas, compounds 29–39. While the parent phenylthiourea, compound 29, had much higher affinity for alpha$_1$-adrenoceptors than prazosin, unfortunately, this compound was unique of those tested. Replacement of the sulfur in compound 29 by oxygen to give the urea, compound 39, considerably decreased the affinity. Saturation of the phenyl ring to cyclohexyl, compound 30, also led to a decrease. Other substitutions, compounds 31–37, also decreased the affinity. It is of interest to note that p-azido substitution, which improved the affinity in the cinnamoyl series, compounds 9 and 16, resulted in a decrease in the thiourea series, compounds 29 and 33.

The fifth group included a variety of aromatic compounds. Compound 41 closely resembled the high affinity photolabel for alpha$_1$-adrenoceptors, the only change being that the azido group of the photolabel was replaced by isothiocyanatane. Electronic and steric parameters of these groups are quite similar.

Nevertheless, isothiocyanatane, compound 41, has a much lower affinity. Compound 42 is similar to a successful photochemical probe for alpha$_1$-adrenoceptors. The low affinity of sulfonamides, compounds 43 and 44, suggests that the carboxamide group of prazosin or the thiourea group of compound 29 cannot be replaced in this manner. Additionally, the activated form of orotic acid, compound 45, failed to yield an active compound.

In the sixth group of compounds, bicyclic aliphatic acids were used to replace the furoyl residue of prazosin. Physiological effects of two compounds of this type, one derived from adamantane carboxylic acid and another from bicyclo[2.2.2]oct-2-ene-5-carboxylic acid (unspecified stereochemistry) had been previously evaluated. These compounds have a high affinity, such as compound 46. A prazosin derivative containing bicyclo[2.2.2]octa-2,5-diene-2-carboxylic acid, compound 47, was found to have excellent affinity. This compound has a carbonyl conjugated double bond and thus can covalently add mercaptans, such as cysteine residues. This addition may occur in the interaction of compound 47 with alpha$_1$-adrenoceptors.

The covalent binding of a reactive drug to a receptor may be expected to occur in two consecutive recognition steps, the first being reversible binding of the pharmacophore part of the drug to the binding site of the receptor, followed by covalent bond formation between the reactive part of the drug with an adjacent site on the receptor, a process which leads to irreversible binding. These processes were clearly and thoroughly analyzed on opioid receptors, as reported in *J. Med. Chem.* 1983, 26. 1229; *op. cit.* 1986, 29, 778; *op. cit.* 1986, 29, 1861. The reactive drug must have a high affinity for the receptor, and the reactive residue of the drug must be able to reach a complementary group of the receptor. Nevertheless, the compounds disclosed herein include compounds which fulfill these requirements, such as compound Nos. 6 and 9, but do not attach irreversibly to the receptor, as compound No. 47 does.

BRIEF DESCRIPTION OF THE DRAWINGS

FIG. 1 - Affinity of compound No. 47 at adrenergic binding sites on brain membranes. Membranes from rat brain cortex were prepared and the displacement of either $^3$H-prazosin 0---0, $^3$H-yohimbine △---△ or $^3$H-DHA ●---● by compound No. 47 was measured. $IC_{50}$ values and apparent $K_i$ values was determined as in Table 1. The data in the figure are from a representative experiment which was repeated. Apparent $K_i$ values were $3.44 \times 10^{-9}$M at $^3$H-prazosin, $8.84 \times 10^{-7}$M at $^3$-yohimbine, and 5.91 at $10^{-6}$M at $^3$H-DHA binding sites, respectivley. The results are the averages of two separate experiments.

FIG. 2 - Dose-response of in vitro blockage of $^3$H-prazosin binding sites by compound No. 47. Brain membranes were prepared and preincubated with varying concentrations of compound No. 47 as described for the basic procedure in the Methods. Membrane preparations were then assayed for saturation of $^3$H-prazosin binding. Data were plotted by the method of Scatchard and are the average of eight separate Controls and between two and five separate experiments at each concentration of compound No. 47. Individual experiments varied less than 10% from their average.

DETAILED DESCRIPTION OF THE INVENTION

Thin layer chromatography was performed on precoated silica gel sheets. Silica gel grade H60, 230-400 mesh (Merck Company) was used for the column chromatography. The structure of the compounds was verified in all cases by nuclear magnetic resonance spectra which were measured at 60 MHz on a JEOL PMX-60 spectrometer in deuterochloroform or deuterodimethylsulfoxide using tetramethylsilane as the standard. Melting points were determined with a Fisher-Johns melting point apparatus and are uncorrected.

Preparation of 4-amino-2(4-bicyclo[2.2.2]octa-2,5-diene-2-carboxypiperazin-1-yl)-6,7-dimethoxyquinazoline, compound 47.

A mixture of 3.9 grams (48.6 mmol) 1,3-cyclohexadiene and 2.35 grams (33.5 mmol) propiolic acid was stirred at room temperature for a week. The mixture was then distilled, and the fraction that distilled at 100°-130° C. at 2.5 mm Hg was collected. Short column chromatography (160 grams of silica gel) of this fraction using chloroform-methanol (98:2) as the eluent yielded 3.8 grams of bicyclo[2.2.2]octa-2,5-diene-2-carboxylic acid, a 75% yield. The melting point was 84°-85° C., Rf 0.29 in the same solvent, $1^{H\text{-}NMR}$ (CDC13): 7.35 (dd, 1 H, C=CH), 6.43-6.03 (m, 2 H, CH=CH), 4.22-4.07 (m, 1H, CH-CCOOH), 3.83-3.65 (m, 1 H, CH), 1.31-1.30 (m, 4H, bridge protons) ppm.

The above acid (37.5 mg, 0.25 mmol) was refluxed with 4 mL thionylchloride for two hours, evaporated in vacuo, and the residue was co-evaporated two times with 10 mL toluene. The acid chloride thus obtained was then dissolved in 6 mL dichloromethane and 4 mL ethyl acetate and added to the stirred solution of 4-amino-6,7-dimethoxy-2(piperazin-1-yl)quinazoline (base form, 73 mg, 0.25 mmol). After two hours, the reaction mixture was washed with saturated aqueous sodium bicarbonate solution, then with water, dried with magnesium sulfate, and evaporated. The residue was recrystallized from ethyl acetate/methanol/cyclohexane, yielding 91 mg, or 85%, of compound 47. The mp was 265°-267° C.; Rf 0.44 (dichloromethane/methanol, 9:1); $1^{H\text{-}NMR}$(CDCL$_3$): 6.85 and 6.82 ppm (2s, 2 H, arOmatic protons), 6.43-6.22 (m, 3 H, vinyl protons), 5.41 (broad s, 2 H, NHz), 3.90-3.62 (m, 16 H, OCH$_3$+piperidine protons+methine protons), 1.35 (s, 4 H, bridge protons) ppm. Anal (C$_{23}$H$_{27}$N$_5$O$_3$) 0.5 CH3OH) C, H, N.

Membrane Preparation

Rat brain cortices were homogenized in approximately 30 volumes/wet weight of 50 mM Tris buffer, pH 7.4, containing 10 mM MgCl$_2$ by use of a Polytron (setting 6 for 10 seconds). It should be noted that this buffer was used throughout the experimental procedures. The homogenate was centrifuged at 48,000×g for 10 minutes in a Sorvall RC-5B centrifuge. The resulting pellet was resuspended in buffer by use of a Polytron and recentrifuged. This process was repeated and the pellet was resuspended in approximately 200 volumes for affinity studies or 20 volumes for irreversibility experiments.

Kidney cortices were dissected from the medulla and homogenized with a Polytron in Tris-Mg buffer containing 0.32M sucrose. The homogenate was centrifuged at 300×g for 10 min. The supernatant was recentrifuged at 8,000×g for 15 min. The pellet ws washed again and finally resuspended in Tris-Mg buffer (approximately 15 volumes/g wet weight). Heart ventricles were dissected from the atria and homogenized with a Polytron in 50 mm Tris buffer, pH 7.5, containing 10 mM EDTA and 0.1M sodium perchlorate. The homogenate was centrifuged qt 48,000×g for ten minutes. The pellet was washed twice with Tris-Mg buffer and finally resuspended in 15 volumes/g wet weight of the same buffer. For standard assay procedures, including saturation and affinity studies, these membrane preparations were used at this dilution except for assays of $^3$-prazosine binding, in which case the membranes were further diluted eight-fold.

Irreversibility Experiments

Aliquots of a suspension of membranes (5 ml), prepared as described above, were incubated with either the addition of only buffer (control) or a solution of the tested compound at various concentrations ranging from $1 \times 10^{-10}$ to $1 \times 10^{-5}$ for about 60 minutes at about 30° C. The suspensions were then diluted to approximately 40 mL with buffer, and incubated a further 10 minutes on ice. The membranes were then washed by a series of four centrifugations and resuspensions before they were finally resuspended in approximately 50 mL buffer for assay of saturation of $^3$-prazosin binding.

Several modifications to these basic procedures were performed. (1) The final resuspension of the original membrane preparations as well as the entire preincubation, washing, and assay procedures were carried out in 1 mM Tris buffer, pli 7.4, or 50 mM sodium phosphate buffer, pH 7.2. (2) After the initial preincubation with the prazosin analog and washing, the membranes were treated identically a second time with the compound before assaying for saturation of $^3$-prazosin binding. (3) (−) Epinephrine (100 micromoles) replaced phentolamine as the ligand used to determine non-specific binding of $^3$-prazosin. (4) The ratio of ligand to receptor (absolute amounts) was increased 10- and 100-fold by preincubating a 10- and 100-fold dilution of membrane preparations with the same concentrations of the prazosin analog.

Receptor Assay $^3$-Prazosin binding sites were measured in an assay volume of 1 ml containing the following: $^3$H-prazosin (about 25 Ci/mMol, Amersham, for affinity experiments, 0.05–1.0 nM, 12 different concentrations for saturation experiments); rat cortical membranes, 800 microliters containing approximately 200–300 micrograms membrane protein per assay; and buffer to make 1 ml. For affinity studies, tubes also contained prazosin derivatives (21 different concentrations between $1 \times 10^{-12}$ and $1 \times 10^{-5}$M). Specific binding was defined as the difference between total binding (measured in the absence of any ligand) and non-specific binding (measured in the presence of 10 microM phentolamine). Duplicate tubes were used for each condition. Reaction tubes were incubated for 30 minutes at 30° C., then diluted to 5 ml with ice cold buffer, and filtered under reduced pressure through Whatman GF/C glass fiber filters. The reaction tubes and filters were washed three additional times with buffer. 5 ml of Ready-Solv MP was added to vials containing the filters and radioactivity was measured in a Beckman LS-5800 liquid scintillation system at about 45% efficiency.

Intact Animal Studies

To test the efficacy of the prazosin analog in vivo. a dose of 10 mg/kg of prazosin analog was injected intraperitoneally into rats. Sixteen hours later, the animals were sacrificed, membranes were prepared from various tissues, and assayed for saturation of $^3$-prazosin binding.

Protein was measured by the method of Lowry using bovine serium albumin as a standard. Levels of significance were determined by Student's test.

It was found that compound No. 47 displaced $^3$-prazosin from rat membrane preparations with apparent nanomolar potency, as shown in Table 1. However, it was a much weaker competitor at $^3$-yohimbine and $^3$-DHA binding sites on brain membranes, as shown in FIG. 1, indicating the alpha$_1$-selectivity of this compound. When membranes were preincubated with compound No. 47, washed, and assayed as described in the basic procedure as described above, there was a dose-dependent decrease in the concentration of $^3$-prazosin binding sites without a change in the Kd of the remaining sites up to approximately 50% blockage of binding at 1 micromole of compound No. 47 as shown in FIG. 2. Higher concentrations in the preincubation mixture increased the Kd of the remaining sites without further decreases in the concentrations of receptors. Preincubating heart and kidney membranes with compound No. 47 also led to approximately 40–50% blockade of binding site without changes in Kd values, but spleen membranes exhibited a statistically insignificant 18% decrease in binding sites, as shown FIG. 3. In contrast, brain membranes treated as above with phenoxybenzamine exhibited an approximately 85% blockade of $^3$-prazosin binding sites without significant Kd changes in the remaining sites, as shown in FIG. 4.

This blockade was specific for alpha$_1$-adrenergic binding sites as evidenced by the following experiments:

(1) Prazosin, when added to the preincubation mixture together with compound 47, prevented the decrease in binding sites caused by compound 47 alone. Prazosin alone in a preincubation mixture had no effect on $^3$-prazosin binding, as shown in Table 2.

TABLE II

| | | | | | | Prazosin Analogs |
|---|---|---|---|---|---|---|
| no. | yield, % | mp, °C. | recryst solvent$^a$ | chrom solvent$^b$ | $R_f$ | formula |
| 2$^c$ | 65 | 240–242 | A | I | 0.28 | $C_{18}H_{21}N_7O_3$ |
| 3 | 54 | 250 dec | D | | | $C_{16}H_{20}N_5O_3Br \cdot 0.5NaHCO_3$ |
| 4 | 48 | 263–265 | A | | | $C_{19}H_{23}N_5O_5 \cdot CH_3CH_2OH \cdot H_2O$ |
| 5 | 36 | 230–232 | B | | | $C_{21}H_{25}N_5O_5$ |
| 6$^c$ | 56 | amorphous | | I | 0.48 | $C_{20}H_{25}N_5O_3 \cdot 1.25H_2O$ |
| 7$^c$ | 57 | 229–232 | D | | | $C_{23}H_{27}N_5O_3 \cdot 4H_2O$ |
| 8$^c$ | 59 | 105 | C | I | 0.54 | $C_{22}H_{25}N_5O_4 \cdot 0.5CH_2Cl_2$ |
| 9 | 52 | 240–245 | D | | | $C_{23}H_{25}N_5O_3$ |
| 10 | 65 | 184 | A | | | $C_{23}H_{24}N_5O_3F \cdot 3 H_2O$ |
| 11$^c$ | 73 | 224 | D | I | 0.57 | $C_{23}H_{24}N_5O_3Cl$ |
| 12$^c$ | 58 | 204 | F | I | 0.66 | $C_{23}H_{24}N_5O_3Br$ |
| 13 | 75 | 178 | G | | | $C_{23}H_{24}N_5O_3F \cdot 3H_2O$ |

TABLE II-continued

Prazosin Analogs

| no. | yield, % | mp. °C. | recryst solvent[a] | chrom solvent[b] | $R_f$ | formula |
|---|---|---|---|---|---|---|
| 14 | 69 | 265 | D | | | $C_{23}H_{20}N_5O_3F_5 \cdot 2CH_3OH$ |
| 15[c] | 39 | 255–257 | D | I | 0.48 | $C_{24}H_{27}N_5O_4$ |
| 16[c] | 86 | 185 dec | D | | | $C_{23}H_{24}N_8O_3$ |
| 17 | 37 | 195–200 | I | I | 0.42 | $C_{24}H_{24}N_6O_3S$ |
| 18 | 42 | 250 dec | B | | | $C_{25}H_{27}N_6O_4Br \cdot H_2O$ |
| 19 | 43 | 297 dec | D | | | $C_{28}H_{30}N_6O_6$ |
| 20 | 21 | 235 | A | I | 0.57 | $C_{23}H_{24}N_5O_3F \cdot HCl \cdot 0.5H_2O^d$ |
| 21 | 56 | 135 | B | I | 0.45 | $C_{23}H_{24}N_8O_3 \cdot 0.5CH_3CO_2C_2H_5$ |
| 22 | 58 | 166–169 | B | III | 0.23 | $C_{29}H_{29}N_5O_3 \cdot 0.25CH_3CO_2C_2H_5$ |
| 23 | 54 | 226–229 | D | | | $C_{24}H_{25}N_5O_4 \cdot H_2O$ |
| 24 | 57 | 286 | C | II | 0.34 | $C_{25}H_{25}N_5O_3 \cdot HCl \cdot 0.5CH_2Cl_2$ |
| 25[c] | 42 | 233–235 | G | | | $C_{24}H_{27}N_5O_3$ |
| 26 | 54 | 117–119 | B | I | 0.65 | $C_{23}H_{25}N_5O_4 \cdot H_2O$ |
| 27 | 47 | 112–116 | E | I | 0.56 | $C_{24}H_{33}N_5O_3 \cdot CH_3OH \cdot \frac{1}{4}CH_2Cl$ |
| 28 | 58 | 243–245 | D | | | $C_{23}H_{23}N_5O_3 \cdot 0.75CH_3OH$ |
| 29[c] | 75 | 143–145 | A | | | $C_{21}H_{24}N_6O_2S \cdot 0.5CH_3CH_2OH$ |
| 30 | 67 | amorphous | | I | 0.59 | $C_{21}H_{30}N_6O_2S$ |
| 31 | 96 | 140–141 | G | | | $C_{21}H_{23}N_6O_2FS \cdot CH_3OH$ |
| 32 | 96 | 143 | C | | | $C_{21}H_{19}N_6O_2F_5S \cdot 0.5CH_3CO_2C_2H_5 \cdot 0.5CH_2Cl_2$ |
| 33 | 97 | 172 | D | | | $C_{21}H_{23}N_9O_2S$ |
| 34 | 78 | amorphous | | | | $C_{22}H_{23}N_7O_2S_2$ |
| 35 | 60 | amorphous | | IV | 04.1 | $C_{22}H_{23}N_7O_2S_2 \cdot CH_3OH$ |
| 36 | 50 | 187–190 | | V | 0.40 | $C_{24}H_{28}N_8O_2S_2$ |
| 37 | 81 | 155–158 | A | | | $C_{25}H_{28}N_6O_4S \cdot H_2O$ |
| 38 | 96 | 163 | C | | | $C_{25}H_{26}N_6O_2S \cdot \frac{1}{4}CH_2Cl_2$ |
| 39[c] | 40 | 250 dec | A | | | $C_{21}H_{24}N_6O_3$ |
| 40 | 51 | 230 dec | D | | | $C_{22}H_{24}N_5O_3Cl$ |
| 41 | 40 | 218–225 dec | J | | | $C_{22}H_{21}N_6O_3SI$ |
| 42 | 55 | 245–248 | B | | | $C_{30}H_{36}N_6O_6$ |
| 43[c] | 63 | 241 | D | | | $C_{21}H_{25}N_5O_4S$ |
| 44 | 84 | amorphous | | I | 0.61 | $C_{18}H_{21}N_5O_4S_2$ |
| 45 | 88 | amorphous | | I | 0.62 | $C_{19}H_{19}N_7O_3Cl_2 \cdot 1.25CH_2Cl_2$ |
| 46[c] | 70 | 128–131 | F | I | 0.50 | $C_{22}H_{27}N_5O_3 \cdot CH_2Cl_2$ |
| 47 | 85 | 265–267 | K | I | 0.44 | $C_{23}H_{27}N_5O_3 \cdot 0.5CH_3OH$ |
| 48 | | 245 dec | | | | $C_{23}H_{29}N_5O_3$ |

Figure 5:
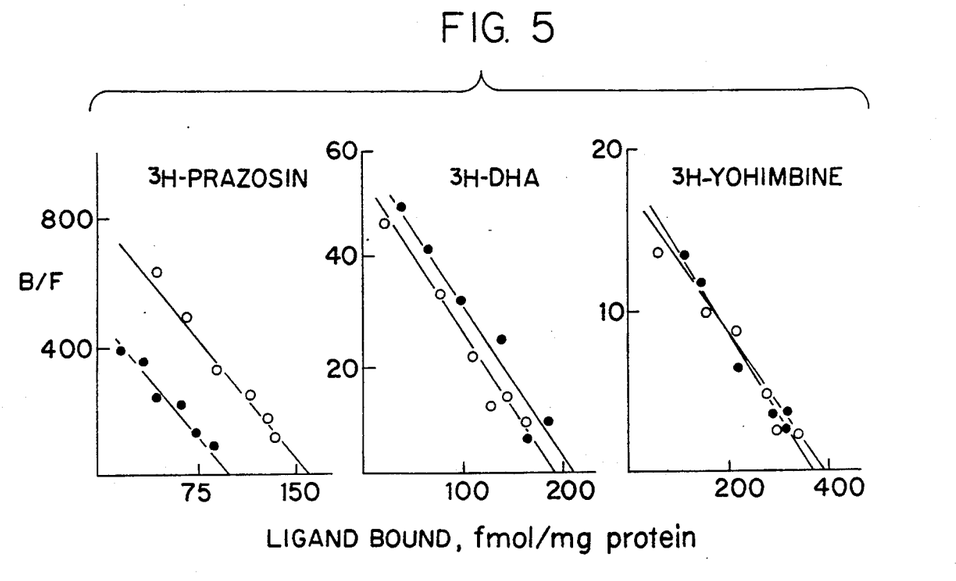
FIG. 5 - In vitro blockage of adrenergic binding sites in rat brain membranes by compound No. b 47 Membranes were preincubated without 0---0, or with 0---0 $1 \times 10^{-7}$M of compound No. 47 and processed as described in the Methods. Membranes were assayed for $^3$-prazosin binding and either $^3$-DHA or $^3$-yohimbine binding. The data are the averages of two separate experiments.

[a] A = aqueous $C_2H_5OH$; B = $CH_3CO_2C_2H_5$; C = $CH_3CO_2C_2H_5$—$CH_2Cl_2$; D = $CH_3CO_2C_2H_5$—$CH_3OH$; E = $CH_3O$-$H$—$CH_2Cl_2$; F = $CH_3CO_2C_2H_5$—$CH_3OH$—$CH_2Cl_2$; G = aqueous $CH_3OH$; I = $C_2H_5OH$-petroleum ether; J = $CH_3CO_2C_2H_5$-petroleum ether; K = $CH_3CO_2C_2H_5$—$CH_3OH$—$C_6H_{12}$.
[b] I = $CH_2Cl_2$—$CH_3OH$, 9:1; II = $CHCl_3$—$CH_3OH$, 92.5:7.5; III = $CH_2Cl_2$—$CH_3CO_2C_2H_5$, 1:1; IV = $CH_2Cl_2$—$CH_3OH$, 92:8; V = benzene-$CH_3OH$, 4:1.
[c] Previously described compounds (2) The binding parameters of $^3$-DHA and $^3$H-yohimbine were unaffected when brain membranes were preincubated with 10 nM of compound 47 and washed as described above, whereas $^3$-prazosin binding was reduced by 50%, as seen in FIG. 5.

Various alterations in the basic protocol to test irreversibility were made in order to obtain assurance that compound 47 was able to block no more than 50% of the $^3$-prazosin binding sites in the brain. Increasing the preincubation time up to three hours did not increase the amount of blockade, cf. FIG. 6. Utilizing 100 microM (−)epinephrine to determine nonspecific binding in the saturation experiments did not change the outcome of the results. Also, substituting lmM Tris buffer, pH 7.4, or 50 mM sodium phosphate buffer, pH 7.2, for Tris-Mg buffer in the preparation of membranes, preincubation and washing procedures, and saturation assays, did not affect the amount of blockade. Increasing the absolute amount of compound No. 47 10- and 100-fold in the preincubation mixture, while keeping its concentration constant (i.e., by diluting the membranes 10- and 100-fold before adding the appropriate concentration of compound 47 for preincubation), did not lead to further blockade. However, the Kd of the remaining receptors increased when lower concentrations of added ligand were used in the diluted preincubation mixtures (i.e., 10 microM compound 47, with standard preincubation volume caused a Kd change; 1 microM of compound 47 at 10×dilution of membranes caused an increase, and 0.1 microM 47 at 100×dilution of membranes caused an increase, and 0.1 microti at.100×dilution of membranes caused an increase).

In another set of experiments, brain membranes, after an initial preincubation with 10 nM of compound No. 47 and washing, were resuspended and preincubated again with 10 nM of compound No. 47, washed, and then assayed for saturation of $^3$-prazosin binding. Even this double incubation of membranes with compound 47 did not increase blockade beyond 50%, as shown in FIG. 7.

To test its efficacy in vivo. compound No. 47 was injected intraperitoneally at a dose of 10 mg/kg into rats. In membranes prepared from brains and hearts of animals 16 hours after injection of compound 47, a 32–44% decrease in Bmax was noted, compared to animals injected with vehicle only. In kidneys, a 21% decrease in Bmax was observed, and a significant increase in the Kd of the remaining receptors was seen, cf. Table 3.

TABLE 3

| | Effect of intraperitoneal injection of Compound 47 into rats. | | | | |
| --- | --- | --- | --- | --- | --- |
| | Control | | Experimental | | % Reduction |
| Tissue | $K_d{}^a$ | $B_{max}{}^b$ | $K_d$ | $B_{max}$ | in $B_{max}$ |
| Brain | 0.317 ± 0.071 | 152 ± 17 | 0.292 ± 0.045 | 104* ± 22 | 36 |
| Heart | 0.150 ± 0.019 | 75.8 ± 11 | 0.255 ± 0.072 | 42.8* ± 5.2 | 43 |
| Kidney | 0.252 ± 0.040 | 61.8 ± 6.1 | 1.24* ± 0.35 | 37.3* ± 9.1 | 21 |

$^a$nM
$^b$fmol/mg protein
*Significantly different from Control at $p < 0.05$.

To compare the effects of prazosin and compound 47 on responses in diastolic blood pressure to the administration of pressor compounds, the following experiments were performed.

Male rats were anesthetized, cannulated, and treated with hexamethonium bromide to block ganglionic effect, and their basal response in blood pressure to pressor compounds was measured. Thereafter, rats were treated intravenously with prazosin (0.11 mg/kg) or compound No. 47 (0.09 mg/kg). After fifteen minutes, the response in blood pressure to pressor compounds was re-evaluated.

After prazosin treatment, a higher concentration of pressor compounds was required to obtain increases in blood pressure. This occurred both for phenylephrine, which is an alpha1-adrenergic acting pressor, and for BHT 933, which is an alpha2-adrenergic pressor. Compound 47 counteracted only to phenylephrine, and not to BHT 933.

Rings from aortas of rabbits were prepared using standard procedures, the rings were characterized, and the effects of compound 47 on contraction caused by norepinephrine were characterized. The effects of exposure of the rings to concentrations of $10^{-6}$M of compound 47 for thirty minutes could not be cancelled by 21 hours of washing at 4° C.

These results were obtained using compound 47, a prazosin analog containing bicyclooctadiene residue. This residue may be replaceable by any other bicycloalkane residue containing one or more double bonds, or by an oxa derivative thereof.

The foregoing description of the specific embodiments will so fully reveal the general nature of the invention that others can, by applying current knowledge, readily modify and/or adapt for various applications such specific embodiments without departing from the generic concept, and therefore such adaptations and modifications are intended to be comprehended within the meaning and range of equivalents of the disclosed embodiments. It is to be understood that the phraseology or terminology employed herein is for the purpose of description and not of limitation.

What is claimed is:

1. A compound having the formula:

(I)

wherein R is —CO-bicyclo[2.2.2]octa-2,5-diene-2-yl or —CO— bicyclo[2.2.2.]oct-2-ene-2-yl.

2. A compound having the formula wherein R is —CO-bicyclo[2.2.2]octa-2,5-diene-2-yl.

3. A compound having the formula:

wherein R is —CO-bicyclo[2.2.2]octa-2-ene-2-yl.

* * * * *